US008424916B2

(12) United States Patent
Shade

(10) Patent No.: US 8,424,916 B2
(45) Date of Patent: Apr. 23, 2013

(54) METHOD FOR CREATING A CUSTOMIZED CHILDREN'S STORYBOOK WITH FINGERPRINT ART USING FINGERPRINT-READY IMAGE TEMPLATES

(76) Inventor: Heather Thompson Shade, San Antonio, TX (US)

(*) Notice: Subject to any disclaimer, the term of this patent is extended or adjusted under 35 U.S.C. 154(b) by 163 days.

(21) Appl. No.: 12/896,062

(22) Filed: Oct. 1, 2010

(65) Prior Publication Data

US 2011/0103920 A1 May 5, 2011

Related U.S. Application Data

(60) Provisional application No. 61/247,938, filed on Oct. 1, 2009.

(51) Int. Cl.
*B42D 15/00* (2006.01)
*G09C 3/00* (2006.01)
*B42C 9/00* (2006.01)

(52) U.S. Cl.
USPC .................................. 283/68; 283/78; 412/1

(58) Field of Classification Search .............. 283/68, 283/78
See application file for complete search history.

(56) References Cited

U.S. PATENT DOCUMENTS

| | | | |
|---|---|---|---|
| 3,408,932 A | 11/1968 | Mucci | |
| 5,114,291 A | 5/1992 | Hefty | |
| 5,213,461 A * | 5/1993 | Kalisher | 412/1 |
| 5,387,107 A | 2/1995 | Gunter et al. | |
| 5,454,600 A * | 10/1995 | Floyd | 283/78 |
| 5,454,678 A * | 10/1995 | Hefty | 412/1 |
| 5,524,932 A | 6/1996 | Kalisher | |
| 5,636,957 A | 6/1997 | Hefty | |
| 5,639,240 A | 6/1997 | Werzberger | |
| 6,210,172 B1 * | 4/2001 | Clements | 434/428 |
| 6,859,211 B2 * | 2/2005 | Friedlander | 434/156 |
| 6,990,476 B2 | 1/2006 | Wen et al. | |
| 7,309,283 B2 | 12/2007 | Nemitz | |
| 2004/0045461 A1 * | 3/2004 | Shade | 283/68 |
| 2005/0202386 A1 * | 9/2005 | Clements | 434/317 |
| 2007/0037129 A1 * | 2/2007 | Boyer | 434/81 |
| 2008/0129033 A1 * | 6/2008 | Anderson et al. | 412/1 |

* cited by examiner

*Primary Examiner* — Dana Ross
*Assistant Examiner* — Kyle Grabowski
(74) *Attorney, Agent, or Firm* — Kammer Browning PLLC

(57) ABSTRACT

Methods for creating customized children's storybooks with fingerprint art using fingerprint-ready image templates stored in association with a software application running on a standard home computer system. The systems and methods include the use of preconfigured templates and prompted discussions that elicit responses from the child to create the text for the storybook. Initially, the appropriate size of the child's fingerprint is determined and the storybook scenes are scaled to fit that size. Fingerprint-ready image templates are used to facilitate the creation of fingerprint art. An image template is formed by including within it at least one fingerprint-sized area. A completed image is formed by inserting a fingerprint into the fingerprint-sized area, and if desired, coloring the image or drawing a scene around the image. In one technique, an entire scene is produced including one or more fingerprint-ready image template(s). When the storybook scenes are completed the software application compiles the book pages and prints the same. The child then personalizes the scene images with their fingerprint and the storybook is bound for repeated reading.

1 Claim, 4 Drawing Sheets

METHOD FOR CREATING A CUSTOMIZED CHILDREN'S STORYBOOK WITH FINGERPRINT ART USING FINGERPRINT-READY IMAGE TEMPLATES

CROSS REFERENCES TO RELATED APPLICATIONS

This application claims the benefit under Title 35 United States Code §119(e) of U.S. Provisional Patent Application Ser. No. 61/247,938; filed: Oct. 1, 2009; the full disclosure of which is incorporated herein by reference.

BACKGROUND OF THE INVENTION

1. Field of the Invention

The present invention relates generally to the creation of books and stories using texts and graphics. The present invention relates more specifically to methods for creating a customized children's storybook with fingerprint art using fingerprint-ready image templates.

2. Description of the Related Art

Without limiting the scope of the invention which is determined solely by the claims, this background information is provided in the context of a specific problem to which the invention in one of its aspects was directed: facilitating the creation of customized children's storybooks using the child's own words and fingerprint art.

Fingerprint art is a popular arts and crafts activity for children. The child places a fingerprint on a piece of paper or other material, and then the child or someone else draws a picture that includes the fingerprint—typically the fingerprint is the body of a figure that is completed with hair, facial features, arms and legs, clothing, etc.

The present Application utilizes in part certain techniques disclosed in U.S. Patent Application Publication No.: US 2004/0045461 A1; Published Mar. 11, 2004; Entitled: Fingerprint Art Using Fingerprint-Ready Image Templates, the full disclosure of which is incorporated in its entirety herein by reference.

A problem with current approaches to fingerprint art is the artistic effort needed to complete the image or scene that includes the fingerprint. On occasion, the child or family would prefer to have a fingerprint image or scene that is beyond the current artistic capabilities of the child, such as to illustrate to the child various techniques that can be used by the child to create fingerprint art.

SUMMARY OF THE INVENTION

An object of the invention is to provide an implement that facilitates fingerprint art. The invention provides methods for using fingerprint-ready image templates. In one aspect, the invention includes an image template defining a fingerprint-ready image, with at least one fingerprint-sized area being defined within the fingerprint-ready image. The fingerprint-ready image is configured to be at least substantially completed by inserting a fingerprint into the fingerprint-sized area.

In an exemplary embodiment, the image template is formed on a stamping implement (such as for use with an inkpad), which is adapted to transfer the fingerprint-ready image template onto paper (or another image surface). Thus, an exemplary method of forming an image is to (a) form (such as by stamping) a fingerprint-ready image that includes at least one fingerprint-sized area within the fingerprint-ready image, and then (b) at least substantially complete the image by inserting a fingerprint into the fingerprint-sized area of the fingerprint-ready image. In an alternate embodiment, one or more image templates are included within a scene.

A better understanding of the features and advantages of the invention will be obtained by reference to the following Detailed Description and accompanying Drawings that set forth an illustrative embodiment based on the principles of the invention.

DETAILED DESCRIPTION OF THE PREFERRED EMBODIMENTS

Process for Creating Children's Storybook

Figure 1:
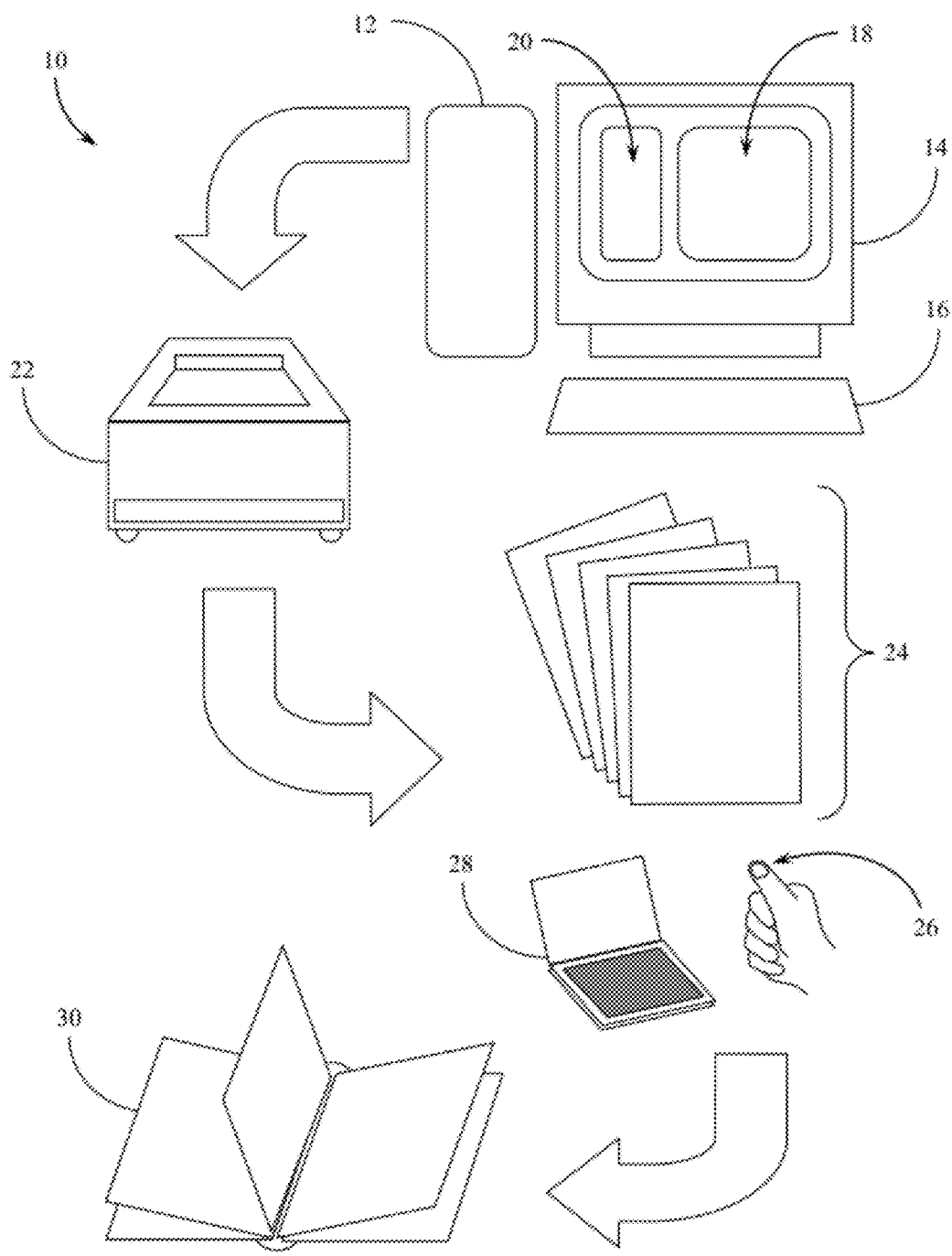
FIG. 1 is a schematic diagram showing a system appropriate for carrying out the method of the present invention as well as the primary steps associated with the method.

The following described process is preferably carried out or followed by a child in the company of an adult. FIG. 1 is a schematic diagram showing a system appropriate for carrying out the method of the present invention as well as the primary steps associated with the method. In general the system 10 comprises the use of a home based computer 12 having the typical display monitor 14 and keyboard input device 16. With the software of the system of the present invention operating on computer 12, two windows are presented on the monitor 14. The first window is a storybook scene preview window 18 and the second is an adult prompt question window 20. Other windows, images, and text are displayed to the users during the operation of the system and method of the present invention. Initially steps are followed to identify the appropriate size of the images to receive the child's fingerprints, a process described in more detail below. Once this sizing routine has been carried out then the process of the present invention proceeds as shown in FIG. 1. As the storybook scene previews 18 are presented on the display 14 the users step through each page (selecting scenes as they go) and then print each page using printer 22 connected to home computer 12. This results in the collection of loose (preferably numbered) printed pages 24 for the various selected storybook scenes, each leaving space (appropriately sized for the child's fingerprint) to allow the child to "personalize" and complete the scenes with their fingerprints. This personalizing step is carried out by having the child ink their finger 26 (which is the thumb in the preferred embodiment, although this is not required) using ink stamp pad 28. After each page 24 has been personalized they are all bound together (in order) to create the bound storybook 30. The binding into book form may be accomplished according to any of a number of know ways of binding (tight or loose) pages of paper together.

Figure 2:
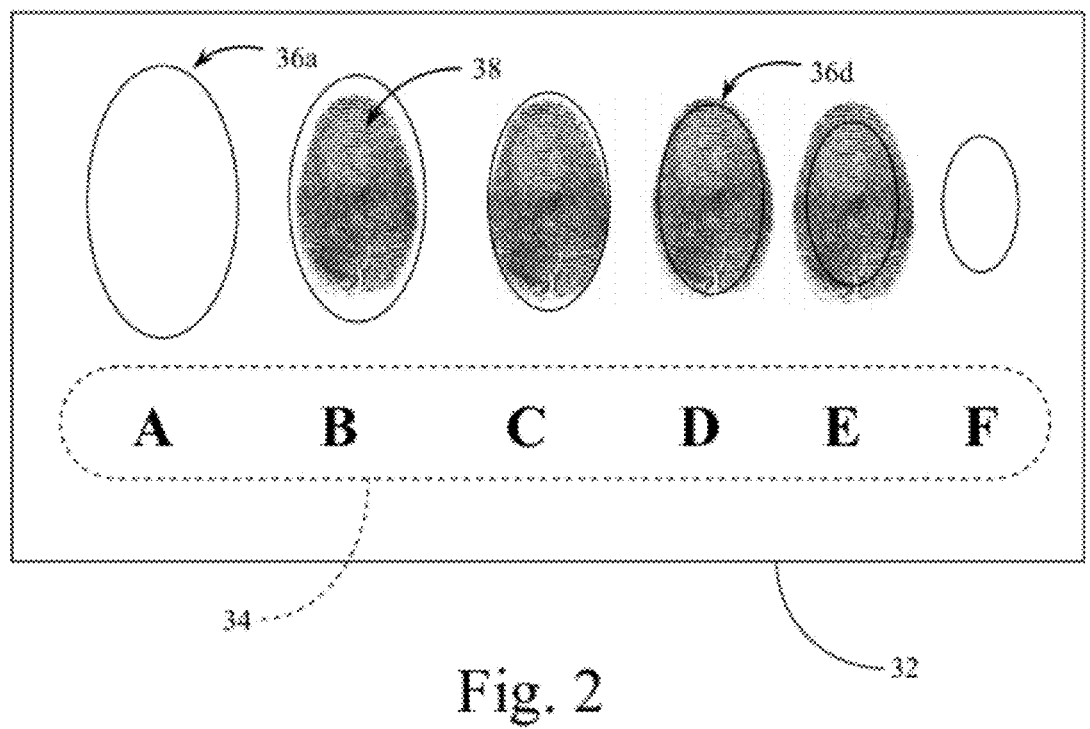
FIG. 2 is a plan view of an example of a fingerprint measurement page generated by the software associated with implementation of the method of the present invention.

Reference is now made to FIG. 2 for a more detailed description of the manner of identifying the size of the child's fingerprint for the purpose of matching (adjusting) the template images created by the software to that child's specific fingerprint size. Using a computer printer, the adult and child print out the finger print measurement page 32. Using an ink pad, the adult and child test the child's fingerprint size in several of the varied sized oval diagrams 36 on the page. From this process the adult and child are able to determine the correct oval size of the child's personal fingerprint 38. The adult and child will then select the corresponding letter (or other indicator) 34 to be input as the proper size for the child's fingerprint when his/her storybook is created.

Figure 4:
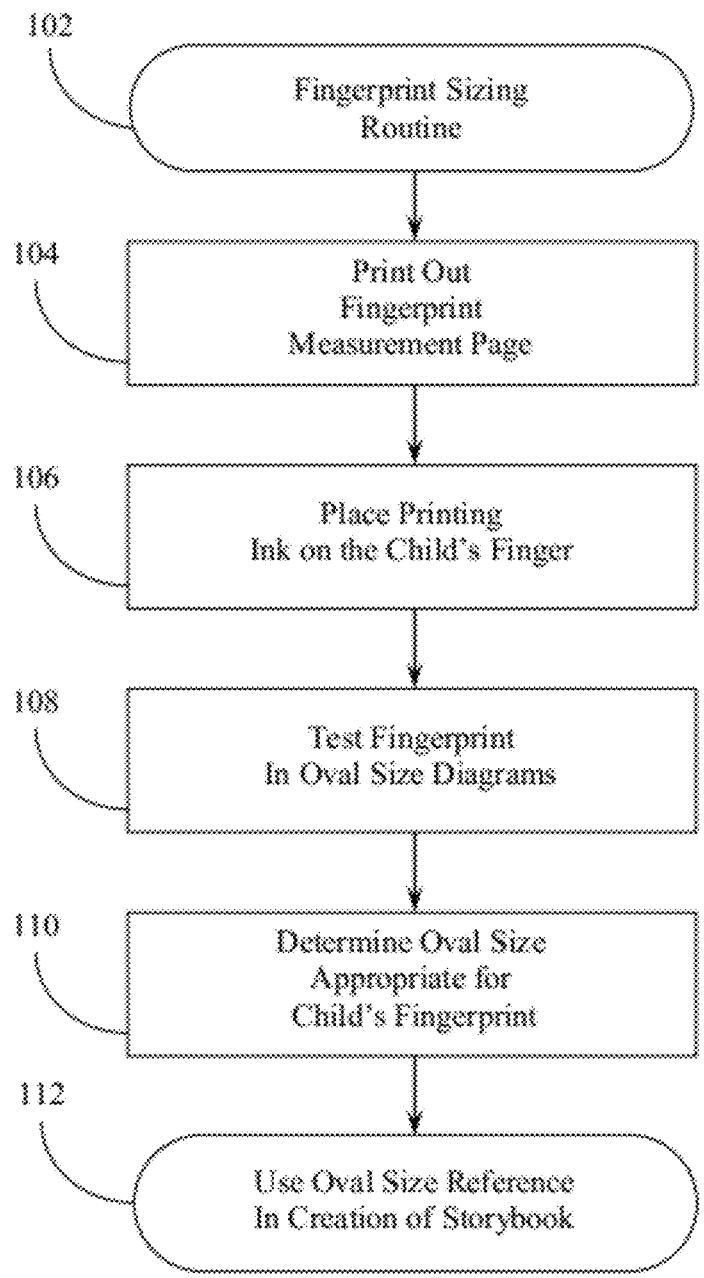
FIG. 4 is a flowchart showing the steps in the process of determining the appropriate size for the fingerprint templates to be used in the creation of the specific child's storybook.

The above described process for determining the size of the child's fingerprint is also described in a step by step manner in FIG. 4. As indicated above, FIG. 4 is a flowchart showing the steps in the process of determining the appropriate size for the fingerprint templates to be used in the creation of the specific child's storybook. Fingerprint sizing routine begins at Step 102 when initiated by the users on the home computer. Step 104 involves printing out the fingerprint measurement page (as seen in FIG. 2). The child's finger is inked at Step 106 followed by imprinting the child's fingerprint on one or more of the test ovals on the measurement page at Step 108. The adult and child then determine, at Step 110, the oval size appropriate for that particular child's fingerprint. Finally at Step 112, the adult and child use the size reference indication (a letter in the example shown in FIG. 2) in the process of creating the storybook template pages at Step 112.

In the process of completing the storybook, the adult and child select a storyline topic from the list of storylines that the child can use to tell a personal experience story about themselves (i.e. nonfiction), or that the child can relate to well enough to create a fictitious story. The computer will then bring up the screen for that selected storyline.

The adult and child then select appropriate scenes from the scene options on the computer screen that support the creation of the storyline. For example, the storyline from the topic "My First Pet" may have several scene choices on the page that tell where the child got their pet. The child may choose the scene from the humane society, or the pet store, or the breeder, or the back alley, etc. to match the story they are creating. There may be several scene options as the storyline progresses.

The adult and child then place the pages in the correct sequence/order to match the child's storyline. The adult will describe and discuss the story with the child as the pages are organized. The adult/child descriptions and discussions will be very helpful in "modeling" the language (sentences) for the child that he/she will soon be speaking to create the storybook.

The adult and child, working together, use the scene on each page to facilitate and support the words that the child will speak as they tell the words/sentence(s) for that page. The parent/adult will use the "prompt" questions and comments provided by the software to assist with eliciting the child's language for the words/sentences that will be typed on each page. The previous two steps will typically happen simultaneously as each page is created.

The adult and child then select graphics using screen "buttons" to choose character features such as hair, facial expressions, glasses, and accessories appropriate to the specific characters and the words used in the story-line as each page is created. The characters will eventually have a generic body comprised of a fingerprint image. These generic fingerprint images will be absent once the storybook is printed. The void spaces left where the generic fingerprints were shown on the computer screen are to be filled in with the child's personal fingerprint when the storybook is printed.

The adult or child will use the text box to type the words/sentences spoken by the child for each page. The text will be entered in the child's simple words/sentences (or a close approximation, thereof) so as to promote a cognitive comfort-level that will: (a) facilitate the child's fluency of thought and (b) encourage literacy-building skills, once the child reads (or follows the book to retell) the story he/she has written.

Once graphics and text are completed in the storybook, the adult uses the computer printer to print the book. The "prompt" questions/comments provided on the screen previously will not appear on the pages of the book. The child then (with the assistance of the adult) uses an ink pad to "ink" the child's finger tip and carefully place it within the open/void space inside each character image on the first page. The adult and child then continue through the pages of the storybook, being sure to "ink" the child's finger for each fingerprint character on each page. The finished storybook pages may then be professionally bound, spiral bound at a local print shop, or simply placed in a ringed binder or similar home-binding device. The adult will want to encourage repeated sharing of the storybook by the child to further develop expressive language skills and to build literacy and cognitive skills.

Figure 3:
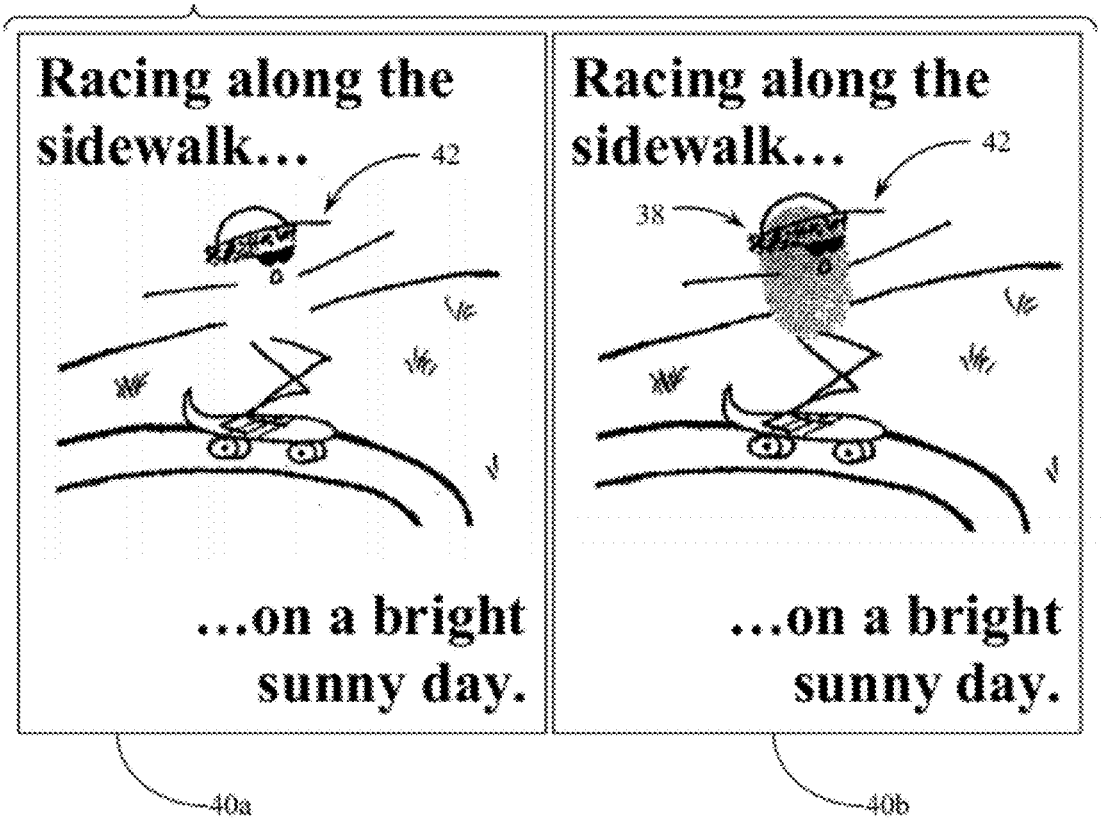
FIG. 3 illustrates an exemplary scene that includes a fingerprint-ready image prior to fingerprint insertion and the same image after fingerprint insertion.
Figure 5:
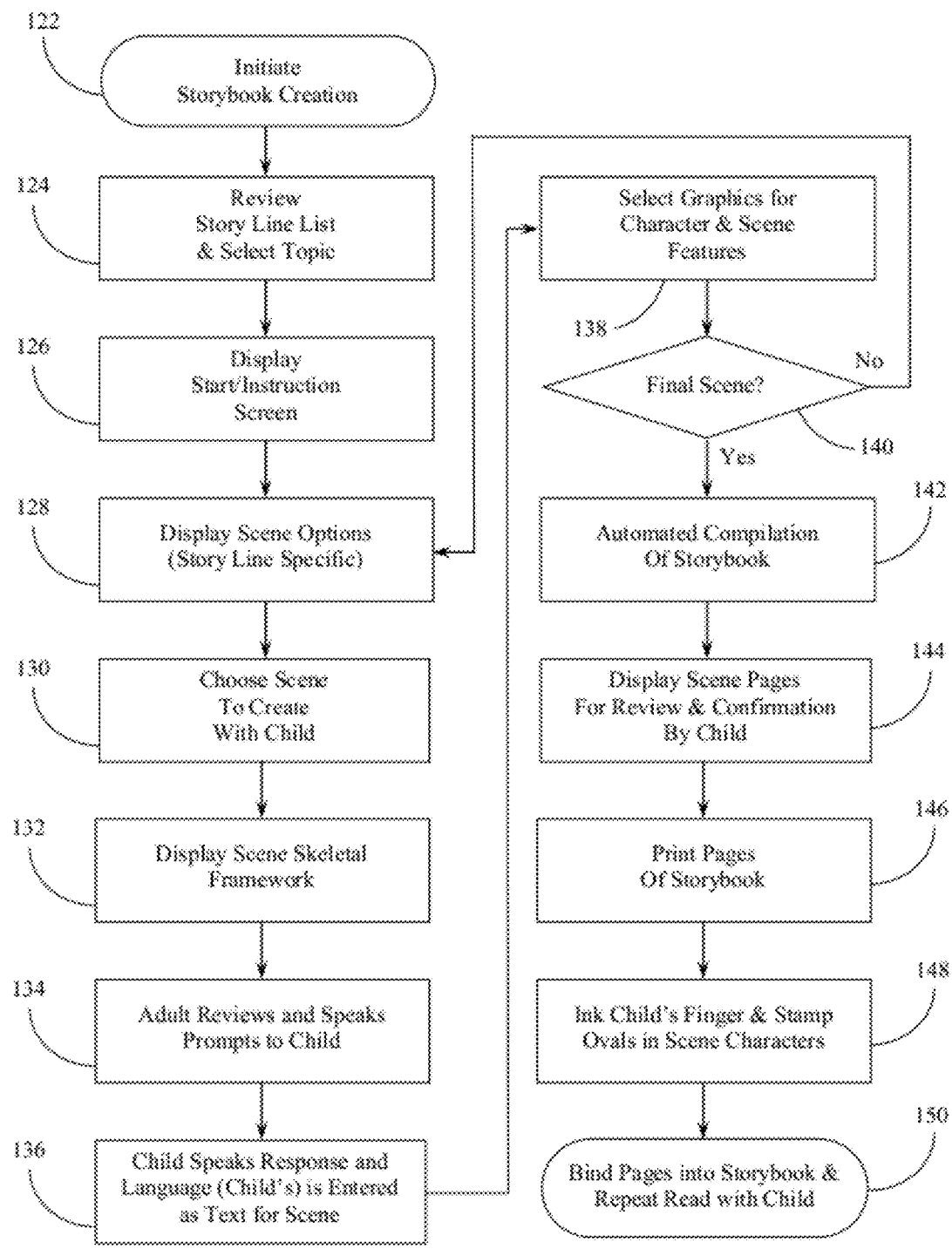
FIG. 5 is a flowchart showing the steps associated with the overall process of creating the children's storybook using the interactive software associated with implementation of the method of the present invention.

The above process is shown structurally by the images presented in FIG. 3 and according to the method steps set forth in the flowchart of FIG. 5. FIG. 3 shows a before and after image of a typical page from the storybook being created. Page 40a is the story scene template page that has been created according to the choices made by the adult and child working together as described above and page 40b is the same page after the child has placed his/her fingerprint 38 on the appropriately sized "body" of the individual 42 in the scene. Although the preferred image uses the child's fingerprint to complete the "body" of the individual in the scene, other objects within the scene may also be constructed to be completed or "personalized" by the use of the child's fingerprint. Insertion of the fingerprint 38 substantially completes the image of a figure on a skateboard (in this example) comprising the fingerprint-ready image 42 and the fingerprint 38. This image can be further enhanced by coloring (after the book pages have been printed) at least portions of the image, and/or adding additional lines to the image, and/or forming a scene which includes the image. Various graphic art software routines may be utilized in some embodiments of the present invention to further embellish the scene although one objective of the present invention is to provide a method that does not require the child or adult to have any specific level of artistic talent or ability to create the scene pages.

The overall method described above is shown in step by step manner in FIG. 5. The storybook creation process is initiated at Step 122. The adult and child review the story line list, at Step 124, and select a topic. The system then displays, at Step 126, a start/instruction screen, primarily for the benefit of the adult. At Step 128, the system then displays various scene option that are story line specific. The adult and child then choose, at Step 130, an individual scene to create. The system displays a skeletal framework for the selected scene at Step 132. The adult reviews and speaks the various prompts to the child at Step 134. The child then speaks a response and the child's language is then entered as text for the scene at Step 136. The adult and child then select the graphics for the character and the scene features at Step 138.

If the adult and child are not creating the final scene in the book (query Step 140) then the process returns to Step 128 where creation of the next scene is initiated. If the final scene has been created then the process proceeds to Step 142 where automated compilation of the storybook by the software of the system of the present invention is carried out. In the preferred embodiment of the present invention, the adult and child are presented with the created storybook pages at Step 144. The adult and child confirm each page (and may preferably be given the opportunity to edit the works). In providing this review presentation the system may insert a placeholder image of a darkened oval to allow for a preview of how the completed page will look.

After the adult and child have confirmed each scene page at Step 144 the process proceeds to Step 146 wherein each of the pages is printed out. The child then (with the help of the adult) then inks his or her finger, at Step 148 and places or stamps his or her fingerprint onto each oval area designated for the same on each of the various storybook scene pages. Finally, at Step 150 the pages of the storybook are bound and the adult and child (or the child alone) re-reads the storybook in its hardcopy form.

Advantages & Features of the System and Method

All of the text is preferably developed by the child, that is, there is no pre-programmed text, thus allowing the child to be the sole author of the book.

The child's original fingerprint is used to finish the scenes, thus allowing for customized artwork of the scenes by the child.

Written prompts are provided (on the computer screen) by the software to the adult throughout the scenes. These prompts effectively elicit the verbalized storyline from the child, thus building expressive language skills and literacy skills as the child repeatedly speaks and reads his/her own familiar words.

The adult and child together will select (from a preprinted page) the correct size of the fingerprint-ready space to be left open/blank/void for the child's personal fingerprint, which will then be adjusted and placed on the finished pages of the storybook. The selection of the specific fingerprint measurement will automatically adjust the size of the graphic image surrounding the void fingerprint-ready space, allowing for an accurate fit between the image and the size of the child's personal fingerprint. One objective is to provide a large enough image that the child will recognize the fingerprint as their own and see its consistency throughout the storybook.

Alternately, the child's actual fingerprint can be downloaded from a biometric fingerprint reading device and placed within the storybook scenes prior to being printed.

The foregoing describes exemplary embodiments of the invention. Various modifications of these embodiments, as well as various alternative embodiments of the invention, will be suggested to those skilled in the art. Thus, it is intended that the claims define the scope of the invention, and that the claims cover all structures and methods, and their equivalents, encompassed by the claims.

ALTERNATE PREFERRED EMBODIMENTS

Various alternate embodiments may implement the basic processes described above. Some of the alternate embodiments may include children's interactive e-books, designed to advance literacy, expressive language, and creative writing skills using the child's developmental level of imagination and cognition. The child would author their very own book and use their very own fingerprints to complete the pictures in their unique story. The parent or adult may print their child's pages for a keepsake and create a treasured learning tool that's filled with personalized memories for both the parent and child.

In summary, the system of the present invention provides for:

(a) "Skeletal" template pages which will combine to create a story as a finished children's book. The book can be printed out from a home computer by the author/creator of the individualized/customized book.

(b) Technology which produces the book electronically (as with an e-book) or from software such as with the creation of a PDF file, or similar digital graphic imagery software.

(c) Pages in the book will allow for manipulation of images/graphics and the creation of text so that the finished story line and graphics are customized by the individual author. A selection of graphics "buttons" will be available to allow various images (i.e. furniture, pets, etc.) and image features (i.e. differing hair, faces, glasses, etc.) to be added to the scenery on each page.

(d) A selection of pages will be available to fit multiple options to the story line (for example, the child chooses getting his puppy from the pound rather than a pet store.)

(e) The application will provide suggested "prompting questions" to aid an adult in helping the child to determine what to say on each page of the story. The adult may input on the computer keyboard (if necessary) the child's text for each page. As an example, prompt: "What did you tell Dad? What did Dad say about your wish?" The adult will say, "Let's put that in your book. What do you want me to type?"

(f) Scenery within the printed pages will leave empty spaces to allow for added customized finishing of the images with fingerprint(s) and/or graphic images that might be created by the child in a personalized manner.

Although the present invention has been described in terms of the foregoing preferred embodiments, this description has been provided by way of explanation only and is not intended to be construed as a limitation of the invention. Those skilled in the art will recognize modifications of various features and structures of the present invention that might accommodate specific computer hardware and software environments. As indicated above, the specific images and text that are utilized are not so important as the ability to personalized the images and text according to the child's interests and desires. These modifications do not necessarily depart from the spirit and scope of the invention.

I claim:

1. A method for creating a customized children's storybook with fingerprint art using fingerprint-ready image templates, the method comprising the steps of:

(a) printing a fingerprint measurement page having a plurality of indexed and variously sized test ovals representative of varying sizes of children's fingerprints;

(b) inking the child's finger and imprinting the child's fingerprint on one or more of the test ovals on the measurement page;

(c) determining the test oval size appropriate for that particular child's fingerprint and noting the size reference index indication for use in creating the storybook;

(d) the child and an assisting adult reviewing a story line list and selecting a topic to be used in the creation of the storybook;

(e) displaying a start/instruction screen followed by various scene options that are story line specific;

(f) the child choosing an individual scene to create;

(g) displaying a skeletal framework for the chosen scene and one or more prompts for the adult to consider, the skeletal framework having one or more template areas positioned within the scene and sized to receive a fingerprint from the child;

(h) the adult reviewing and speaking one or more prompts to the child;

(i) the child speaking a response and the adult entering the child's language as text for the displayed and chosen scene;

(j) the child selecting graphics for a scene character and for additional scene features;

(k) if not creating the final scene in the storybook, repeating the steps of choosing a scene, displaying a skeletal framework, reviewing and speaking prompts, entering text, and selecting graphics;

(l) after creating the final scene in the storybook, automatically compiling the storybook in digital form;

(m) displaying the digital form of the created storybook and confirming each page;

(n) printing each of the created scene pages of the storybook;

(o) inking the child's finger and stamping the child's fingerprint onto each oval template areas designated for the same on each of the various storybook scene pages;

(p) binding the pages of the storybook; and (q) reading the storybook in its hardcopy form.

* * * * *